United States Patent
Zhang et al.

[11] Patent Number: 6,051,597
[45] Date of Patent: Apr. 18, 2000

[54] INDOLYLQUINONES AS ANTIDIABETIC AGENTS

[75] Inventors: Bei Zhang, Edison, N.J.; Royo Inmaculada; Fernando Pelaez, both of Madrid, Spain; Gino M. Salituro, Fanwood; Gerald F. Bills, Clark, both of N.J.

[73] Assignee: Merck & Co., Inc., Rahway, N.J.

[21] Appl. No.: 09/095,244

[22] Filed: Jun. 10, 1998

Related U.S. Application Data

[60] Provisional application No. 60/049,545, Jun. 13, 1997.

[51] Int. Cl.$^7$ .................................................. A61K 31/40
[52] U.S. Cl. ............................................. 514/414; 514/415
[58] Field of Search ....................................... 514/414, 415

[56] References Cited

U.S. PATENT DOCUMENTS

| | | | |
|---|---|---|---|
| 5,409,949 | 4/1995 | Buzzetti et al. | 514/414 |
| 5,780,496 | 7/1998 | Tang et al. | 514/414 |
| 5,786,488 | 7/1998 | Tang et al. | 548/455 |
| 5,849,710 | 12/1998 | Battistini et al. | 514/18 |

FOREIGN PATENT DOCUMENTS

WO 96/40115  12/1996  WIPO.

OTHER PUBLICATIONS

Arai, et al, Chem. Pharm. Bull, 1981, 29(4):961–969, 991–999.
Shimizu, et al, Gann, 1982, 73:642–648.
Mocek, et al, J. Antibiotics, 1996, 49(9):854–859.
Shimizu, et al, Chem. Pharm. Bull., 1982, 30(5):1896–1899.
Arai, et al, Chem. Pharm. Bull, 1990, 38 (11):2929–2932.
Kaji, et al, Chem. Pharm. Bull, 1996, 44 (2):2340–2341.
Kaji, et al, Chem. Pharm. Bull, 1994, 42 (8):1682–1684.
Kaji, et al, Chem. Pharm. Bull, 1995, 43 (10):1818–1820.

*Primary Examiner*—James H. Reamer
*Attorney, Agent, or Firm*—James L. McGinnis; David L. Rose; Mollie M. Yang

[57] ABSTRACT

Indolylquinones are useful for the treatment and prevention of diabetes mellitus, and in particular, for the treatment or prevention of hyperglycemia in diabetic patients. Some of the indolylquinones are produced by fermentation of the novel fungus Pseudomassaria sp. ATCC 74411.

8 Claims, No Drawings

INDOLYLQUINONES AS ANTIDIABETIC AGENTS

CROSS REFERENCE TO RELATED APPLICATION

This application is based on, and claims priority from, provisional application number 60/049,545 filed Jun. 13, 1997.

SUMMARY OF THE INVENTION

The present invention provides a method for the treatment of conditions in which levels of insulin, biological activity of insulin, levels of insulin sensitivity, or a combination thereof, have been altered such as in diabetes mellitus. In particular, the present invention provides a method for the treatment or prevention of diabetes mellitus, hyperglycemia, or for controlling blood glucose level in an animal. The present invention also provides novel compounds useful in the method of treatment, as well as phamaceutical compositions containing such compounds. Also included in the present invention are novel microorganism for producing compounds useful in the present method, and fermentation process for producing such compounds.

BACKGROUND OF THE INVENTION

Insulin is a hormone that is necessary for normal carbohydrate, protein, and fat metabolism in mammals. All known actions of insulin are initiated by binding of the hormone to the extracellular domain ($\alpha$-subunits) of its specific receptor. Following insulin binding, conformational changes in the insulin receptor lead to autophosphorylation of the intracellular $\beta$-subunits and stimulation of the receptor's intrinsic tyrosine kinase activity and activation of insulin signal transduction pathway. The activated insulin receptor tyrosine kinase phosphorylates several immediate substrates (e.g. IRS-1 and SHC). These proximal events lead to activation of additional signaling intermediates such as PI-3-kinase and MAP kinase. Through an unknown series of additional steps, modulation of key cellular components (e.g. glucose transporter translocation, activation of glycogen synthase, inhibition of gluconeogenic enzymes) coordinate stimulation of glucose disposal and inhibition of hepatic glucose output. Considerable evidence suggests that insulin receptor tyrosine kinase activity is essential for many, if not all of the biological effects of insulin. However, the precise biochemical mechanisms linking receptor kinase-mediated tyrosine phosphorylation to the regulation of cellular metabolic pathways are not completely defined.

Two major forms of diabetes mellitus are now recognized. Type I diabetes, or insulin-dependent diabetes, is the result of an absolute deficiency of insulin, the hormone which regulates glucose utilization, and patients with Type I diabetes are dependent on exogenous insulin for survival. Type II diabetes, or non-insulin-dependent diabetes (NIDDM), often occurs in the face of normal, or even elevated levels of insulin and appears to be the result of the inability of tissues to respond appropriately to insulin (i.e. insulin resistance). Insulin resistance is a major susceptibility trait for NIDDM and is also a contributing factor in atherosclerosis, hypertension, lipid disorders, and polycystic ovarian syndrome.

Over time, many individuals with type II diabetes show decreased insulin production, which requires supplemental insulin for adequate blood glucose control, especially during times of stress or illness. An exogenous insulin regimen is often required in the treatment of secondary diabetes, i.e., diabetes occurring in relation to other disease states such as pancreatic disease. Insulin is also used in some cases of gestational diabetes to obtain optimum blood glucose control. The conventional route of insulin administration is via a needle and syringe. Continuous subcutaneous insulin infusion with an infusion pump is an alternative to conventional injection therapy for achieving normalized levels of blood glucose.

The several treatments for NIDDM, which has not changed substantially in many years, are all with limitations. While physical exercise and reductions in dietary intake of calories could improve the diabetic condition, compliance with this treatment is generally poor. Increasing the plasma level of insulin by administration of sulfonylureas (e.g. tolbutamide, glipizide) which stimulate the pancreatic $\beta$-cells to secrete more insulin or by injection of insulin after the response to sulfonylureas fails will result in high enough insulin concentrations to stimulate the very insulin-resistant tissues. However, dangerously low levels of plasma glucose can result from these last two treatments and increasing insulin resistance due to the even higher plasma insulin levels could theoretically occur. The biguanides increase insulin sensitivity resulting in some correction of hyperglycemia. However, the two biguanides, phenformin and metformin, can induce lactic acidosis and nausea/diarrhea, respectively.

The thiazolidinediones (glitazones) are a more recently described class of compounds with potential for a novel mode of action in ameliorating many symptoms of NIDDM. These agents substantially increase insulin sensitivity in muscle, liver and adipose tissue in several animal models of NIDDM resulting in complete correction of the elevated plasma levels of glucose, triglycerides and nonesterified fatty acids without any occurrence of hypoglycemia. However, undesirable effects associated with the glitazones have occurred in animal and human studies including cardiac hypertrophy, hemadilution and liver toxicity.

Accordingly, there exists a continuing need for novel therapeutic agents for ameliorating the symptoms of diabetes mellitus, particularly for controlling the blood glucose level in patients, and for the prevention of the onset of diabetes. In addition, there is a need for new therapeutic agents for treating or overcoming insulin resistance in cases where it contributes to the pathogenesis of diseases or disorders.

The compounds used in the present invention belong to a class of compounds generally known as asterriquinones, which are characterized as 2,5-dioxy-3,6-bis(indolyl) quinones. A number of asterriquinones have been reported in the literature as having antitumor activity. Asterriquinone B1 (compound Ia, infra), demethyl asterriquinone B1 (compound Ib, infra), and their respective hydrogenated products (compounds Ic and Id, infra) are disclosed in Arai et al, *Chem. Pharm. Bull.*, 1981, 29(4):961–969; Arai et al, *Chem. Pharm. Bull.*, 1981, 29(4):991–999; and Shimizu et al, *Gann*, 1982, 73:642–648.

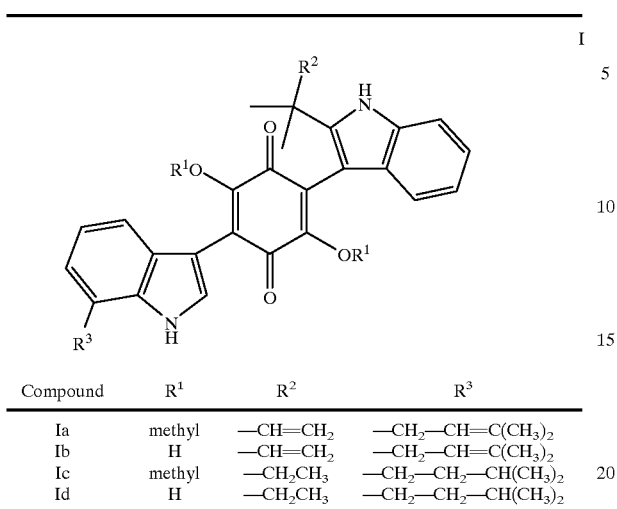

| Compound | R¹ | R² | R³ |
|---|---|---|---|
| Ia | methyl | —CH=CH₂ | —CH₂—CH=C(CH₃)₂ |
| Ib | H | —CH=CH₂ | —CH₂—CH=C(CH₃)₂ |
| Ic | methyl | —CH₂CH₃ | —CH₂—CH₂—CH(CH₃)₂ |
| Id | H | —CH₂CH₃ | —CH₂—CH₂—CH(CH₃)₂ |

Asterriquinones having a 3-methyl-1,3-butadienyl side chain are reported in Mocek et al, *J. Antibiotics,* 1996, 49(9):854–859, as inhibitors of serine proteases of the coagulation pathway.

In PCT Application WO96/40115 indolylquinones are disclosed as inhibitors of adaptor protein/tyrosine kinase interactions.

DETAILED DESCRIPTION OF THE INVENTION

The present invention provides a method for the treatment or prevention of conditions in an animal in which levels of insulin, biological activity of insulin, levels of insulin sensitivity, or a combination thereof, have been altered, which comprises administering to said animal a therapeutically effective amount of an asterriquinone capable of modulating insulin receptor tyrosine kinase activity.

The present invention also provides a method for treating or preventing the onset of diabetes mellitis in an animal which comprises administering to said animal a therapeutically effective amount of an asterriquinone capable of modulating insulin receptor tyrosine kinase activity.

The present invention further provides a method for reducing blood glucose level in an animal in need of such reduction which comprises administering to said animal a glucose reducing effective amount of an asterriquinone capable of modulating insulin receptor tyrosine kinase activity.

In one embodiment of the afore-mentioned methods, the asterriquinone is a compound having the formula I:

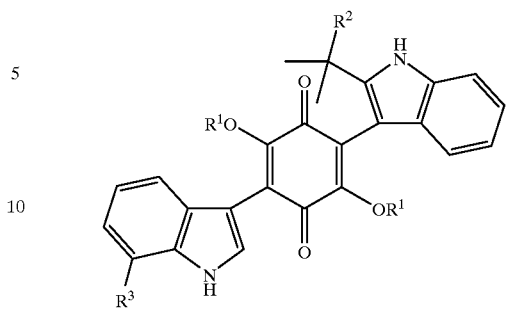

wherein
R¹ is hydrogen or methyl;
R² is —CH₂CH₃ or —CH=CH₂;
R³ is —CH=CH—C(CH₃)=CH₂; —CH₂—CH=C(CH₃)₂ or —CH₂—CH₂—CH(CH₃)₂;
or a pharmaceutically acceptable salt thereof. In a preferred embodiment R¹ is hydrogen; in another preferred embodiment R² is —CH=CH₂; in yet another preferred embodiment R³ is —CH₂—CH=C(CH₃)₂.

Another aspect of the present invention provides novel compounds Ie and If:

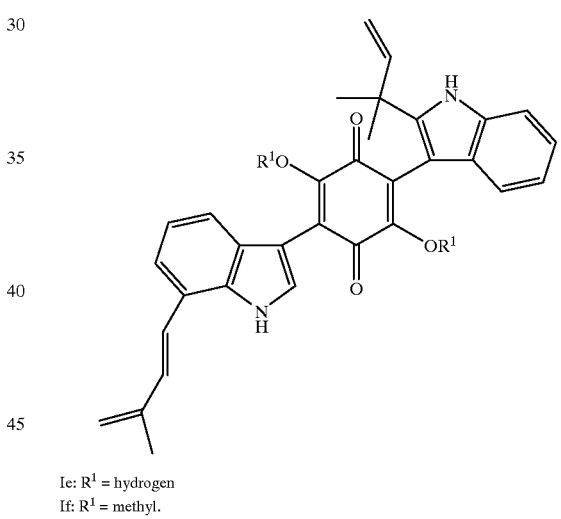

Ie: R¹ = hydrogen
If: R¹ = methyl.

Yet another aspect of the present invention provides pharmaceutical compositions containing a compound of formula I and a pharmaceutically acceptable carrier.

In another aspect of the present invention there is provided a process for the preparation of a compound of formula Ib or Ie which comprises cultivating a strain of Pseudomassaria sp. having the identifying characteristics of ATCC 74411 and capable of producing said compound, in a nutrient medium containing assimilable sources of carbon and nitrogen, and recovering said compound.

Another aspect of the present invention provides a biologically pure culture of the fungus Pseudomassaria sp. ATCC No. 74411.

As used herein, the term "asterriquinone" means compounds having the following core structure in which the carbon and nitrogen atoms of the indole rings, and the oxygen atoms are optionally substituted:

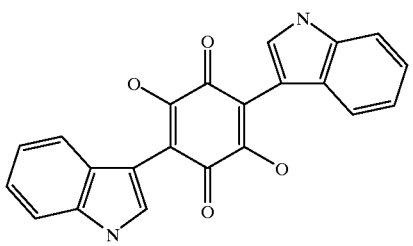

Many asterriquinones have been reported in the literature, including:
1) Arai et al, *Chem. Pharm. Bull.*, 1981, 29(4):961–969;
2) Arai et al, *Chem. Pharm. Bull.*, 1981, 29(4):991–999;
3) Shimizu et al, *Gann*, 1982, 73:642–648;
4) Mocek et al, *J. Antibiotics*, 1996, 49(9):854–859;
5) Shimizu et al, *Chem. Pharm. Bull.*, 1982, 30(5):1896–1899;
6) Arai et al, *Chem. Pharm. Bull.*, 1990, 38(11):2929–2932;
7) Kaji et al, *Chem. Pharm. Bull.*, 1996, 44(2):2340–2341;
8) Kaji et al, *Chem. Pharm. Bull.*, 1994, 42(8):1682–1684;
9) Kaji et al, *Chem. Pharm. Bull.*, 1995, 43(10):1818–1820;
10) Tang et al, PCT Published Application WO96/40115, published Dec. 19, 1996.

The term "to modulate insulin receptor tyrosine kinase activity" includes activating insulin receptor tyrosine kinase, stimulating insulin receptor tyrosine phosphorylation, or enhancing the effect of insulin to stimulate insulin receptor tyrosine kinase activity or insulin signal transduction pathway. The ability of an asterriquinone to modulate insulin receptor tyrosine activity may be determined using the methods described in Examples 6 and 7 hereinbelow. Briefly, Chinese Hamster Ovary (CHO) cells expressing human insulin receptor are plated and treated with insulin and/or test agents. CHO.T cells are one type of CHO cells that express human insulin receptor. The treated cells are lysed, and the insulin receptor is purified. The level of tyrosine phosphorylation of the receptor is determined using an anti-phosphotyrosine antibody conjugated to alkaline phosphatase and its chromogenic substrate. The insulin receptor tyrosine kinase activity (IRTK) is determined using an exogenous substrate and $\gamma$-$^{32}$P-ATP. Although the procedures described in the Examples utilize CHO.T cells, which are available from Dr. Richard Roth of Stanford University, cell lines similar to the CHO.T cells used herein may be prepared by one skilled in the art. For example, NIH3T3 cells, COS cells, Rat-1 cells and other appropriate fibroblasts transfected with cDNA encoding human insulin receptor can also be used in the assays.

The concept of altered levels of insulin, biological activity of insulin, levels of insulin sensitivity includes impaired insulin production and/or activity, lower than normal levels of endogenous insulin, resistance to normal or elevated level of insulin, which may be due to insufficient insulin receptor expression, reduced insulin-binding affinity, or any abnormality at any step along the insulin signaling pathway.

Compounds Ib and Ie are produced by the fermentation of the fungus Pseudomassaria sp. (Ascomycotina, Hyponectriaceae), (Merck Culture Number MF6301) isolated from leaf litter collected in Kinshasa, Zaire (Democratic Republic of Congo). A culture of this organism has been deposited with the American Type Culture Collection (Rockville, Md., USA) on May 9, 1997 under the BUDAPEST TREATY ON THE INTERNATIONAL RECOGNITION OF THE DEPOSIT OF MICROORGANISMS FOR THE PURPOSES OF PATENT PROCEDURE and assigned the accession number ATCC 74411.

Producing Organism

In agar culture, colonies of the fungus MF6301 (ATCC 74411) exhibit the following characteristics:

Colonies on oatmeal agar (R. B. Stevens. 1981. Mycology Guidebook. University of Washington Press, medium M-15) at 23 C, 12 hr photoperiod, growing slowly, attaining 85 mm diameter in 28 days, with margin even to undulating, with aerial mycelium velvety, azonate, white to dull pinkish gray Light Cinnamon Drab, Light Drab (capitalized color names from Ridgway, R. 1912. Color Standards and Nomenclature. published by the author. Wash., DC), or cinnamon, with reverse accumulating a dark brown pigment, with mycelium causing cerebriform buckling of the medium. Odors absent, exuding drops of clear brown liquid.

Colonies on YME agar (Difco malt extract 10 g, Difco yeast extract 4 g, glucose 4 g, agar 20 g, 1 L $H_2O$) at 23 C, 12 hr photoperiod, growing slowly, attaining 80–85 mm diameter in 28 days, appressed, undulating or fimbriate at the margin, raised towards the center, velvety to woolly, obscurely zonate, collapsing with age, pale buff Drab, to dark brown, Benzo Brown, Dusky Drab, Fucous, brownish black, Blackish Brown (2) in reverse. Odors absent, exuding drops of clear brown liquid and a dark reddish brown soluble pigment.

Reproductive structures were never observed to form in agar culture. To induce sporulation, the fungus was cultivated on wood. Four 1-cm agar plugs from YME plates were placed in a 50 ml of a dilute malt yeast extract broth (1 g malt extract, 0.5 g yeast extract, 1 L $H_2O$) with 6 strips of wood of *Robinia pseudoacacia*, approximately 4×1×0.5 cm. The broth was agitated on a gyrotary shaker (23 C, 220 rpm, 7 days) until growth was evident. Wood pieces were removed and incubated on water agar (23 C, 12 hr photoperiod, under fluorescent and near ultraviolet light). After two week white ascomal initials were evident on wood of *Robinia pseudoacacia*. From several dozen initials, a single fertile ascoma was observed. This technique was also attempted with wood of *Betula papyrifera*, although ascomal initials formed abundantly, they never matured.

The fungus produced only sparse cottony mycelium on the wood fragments. After 3–4 weeks, white, cottony, spherical to subspherical structures developed among the mycelia. The largest and most pigmented of these structures was dissected from the wood and examined microscopically and found to contain asci and ascospores. It is quite likely that this was not a mature ascoma, since no dehiscence mechanism was had obviously developed and few free ascospores were evident. Therefore, the following description and taxonomic evaluation must be viewed as being preliminary because only a single, possibly immature, ascoma was examined.

Ascoma apparently cleistothecial, superficial, partly enveloped in white, cottony mycelium, lacking stromatic tissues, up to 800 μm in diameter, subglobose, non-ostiole, unilocular, solitary to confluent, covered with a thin, cottony layer of white mycelium, dark gray to black beneath mycelial layer. Ascoma wall a textura intricata to textura angularis, composed of densely interwoven hyphae and dark irregular plate-like cells, often with adhering vegetative hyphae.

Asci arising from a central basal region of the centrum, clavate to cylindrical, 70–75×15–20 μm, unitunicate, 8-spored, uniseriate, with a distinct apical ring, with apex broadly rounded. Ascospores 17–19×8–10 μm, ellipsoidal, 2-celled, with upper cell broadly elliptical, 14–16.5 μm long, with lower cell subconical or triangular in side view, 3–4 μm long, usually eccentric with respect to larger cell, often constricted at the septum, sometimes with a thin gelatinous sheath, hyaline, but lack of pigment possibly maybe due to immaturity.

Mycelium composed of highly branched, simple septate, hyaline to dematiaceous hyphae characteristic of many ascomycetous fungi.

Following the classification scheme of von Arx (J. A. von Arx. 1981. The Genera of Fungi Sporulating in Pure Culture. J. Cramer, Vaduz, Germany), MF6301 is tentatively identified as a species of Pseudomassaria on the following basis: cleistothecial ascoma, or least non-ostiolate, with a membranous wall composed of flattened angular cells; persistent clavate to cylindrical asci that have a conspicuous apical ring; ascospores without apical pores or germs slits; 2-celled ascospores with the lower cell decidedly smaller; and ascospores light-colored with an apparent gelatinous sheath. The ascospore size of MF6301 falls within the range of many of species of Pseudomassaria described by Barr (M. E. Barr. 1964. The Genus Pseudomassaria in North America. Mycologia 56:841–862). The occurrence of MF6301 on decaying vegetation is also consistent with habitat of many species of Pseudomassaria.

Fermentation Process

Compounds of formula Ib and Ie are produced by cultivating a strain of Pseudomassaria sp. capable of producing said compound on a conventional solid medium or in a conventional aqueous medium. The organism is grown in a nutrient medium containing known nutritional sources for similar fungi, i.e. assimilable sources of carbon and nitrogen plus optional inorganic salts and other known growth factors. The general procedures used for the cultivation of other similar fungi are applicable to the present invention.

The nutrient medium should contain an appropriate assimilable carbon source such as ribose, glucose, sucrose, cellobiose and fructose. As nitrogen source, ammonium chloride, ammonium sulfate, urea, ammonium nitrate, sodium nitrate, etc. may be used either alone or in combination with organic nitrogen sources such as peptone, fish meal extract, yeast extract, corn steep liquor, soybean powder, cotton seed flour, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

Production of the compounds may be effected at any temperature conducive to satisfactory growth of the producing organism, e.g. 20°–30° C. For Pseudomassaria sp. ATCC 74411, the production temperature is preferably at about 25° C. Ordinarily, optimum production of the desired compound is obtained in shake flasks after incubation periods of 10–21 days. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from a slant culture or a lyophilized culture of the organism. After obtaining an active inoculum in this manner, it is aseptically transferred to the fermentation tank medium. Production of the desired compound in tank fermentors usually reaches the optimum after 7 to 21 days of incubation. Agitation in the tank fermentor is provided by stirring and aeration may be achieved by injection of air or oxygen into the agitated mixture. Compound production may be monitored using chromatographic or spectroscopic techniques, or by a conventional biological assay.

Isolation and Purification

Compounds of formula Ib and Ie are readily recovered from fermentation broth by extracting the whole broth with an organic solvent such as methyl ethyl ketone. The compounds may be purified using standard methods well known in the art such as gel filtration chromatography, thin layer chromatography, high performance liquid chromatography, concentration, precipitation and/or crystallization, or combinations thereof. Alternatively, the whole broth or an organic extract thereof may be spray-dried or freeze-dried, followed by purification as above mentioned.

Chemical Transformation

Compounds Ib and Ie may be converted to other compounds within the scope of formula I. Thus treatment of compound Ib or Ie with diazomethane produces the corresponding compound in which $R^1$ is methyl. Catalytic hydrogenation of compounds Ib, Ie, or their corresponding methyl ethers, followed by oxidation, leads to compounds of formula I in which the $R^2$ and $R^3$ sidechains are fully saturated.

Utility

Asterriquinones capable of modulating insulin receptor tyrosine kinase activity (also referred to herein as active asterriquinones) are useful in the treatment, prevention, amelioration, suppression or control of diseases, disorders or conditions that are characterized by altered insulin levels, biological activity of insulin, insulin sensitivity, or a combination thereof. Such diseases or disorders include diabetes mellitus (Type I and Type II), atherosclerosis, hypertension, lipid disorders, polycystic ovarian syndrome, and other conditions associated with insulin deficiency or insulin resistance. These compounds are also useful in the treatment or prevention of hyperglycemia or for controlling blood glucose levels in an animal suffering from Type I or Type II diabetes mellitus.

Without being bound by theory, it is believed that active asterriquinones assert their pharmacological effects by stimulating insulin receptor tyrosine kinase activity. In addition, these compounds stimulate tyrosine phosphorylation of insulin receptor β subunit and insulin receptor substrate-1 as well as activity of phosphoinositide-3-kinase. These compounds have the properties of an insulin mimetic and sensitizing agent.

Dose Ranges

The effective dosage of active ingredient employed may vary depending on the particular compound employed, the mode of administration, the condition being treated and the severity of the condition being treated. Although active asterriquinones may be administered by any conventional mode of administration, including intravenous, intramuscular, subcutaneous, oral, topical, etc.; oral administration is preferred.

When treating or preventing diabetes mellitus and/or hyperglycemia generally satisfactory results are obtained when the active asterriquinones of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Composition

Another aspect of the present invention provides pharmaceutical compositions which comprises an active asterriquinone and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise an active asterriquinone as an active ingredient, and may also contain a pharmaceutically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, an active asterriquinone can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, the active ingredient may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

Combination Therapy

Asterriquinones of the present invention may be used in combination with other drugs. Such other drugs may be administered, by a route and in an amount commonly used therefor, contemporaneously or sequentially with an asterriquinone. When an asterriquinone is used contemporaneously with one or more other drugs, a pharmaceutical composition containing such other drugs in addition to the asterriquinone is preferred. Accordingly, the pharmaceutical compositions of the present invention include those that also contain one or more other active ingredients, in addition to an asterriquine. Examples of other active ingredients that may be combined with an active asterriquinone, either administered separately or in the same pharmaceutical compositions, include, but are limited to antidiabetic agents such as insulin, sulfonylureas, biguanides (such as metformin) α-glucosidase inhibitors (such as acarbose), and peroxisome proliferator-activater receptor γ agonists such as the glitazones (thiazolidinediones such as pioglitazone, troglitazone, MCC-555, and BRL49653); cholesterol lowering agents such as HMG-CoA reductase inhibitors (lovastatin, simvastatin and pravastatin, fluvastatin, atorvastatin, and other statins), sequestrants (cholestyramine, colestipol and a dialkylaminoalkyl derivatives of a cross-linked dextran), nicotinyl alcohol nicotinic acid or a salt thereof, proliferator-activater receptor α agonists such as fenofibric acid derivatives (gemfibrozil, clofibrat, fenofibrate and benzafibrate), and probucol.

EXAMPLE 1.

(a) Seed Culture of Pseudomassaria sp. ATCC 74411

Culture MF6301 (ATCC 74411) was grown on Difco Potato Dextrose Agar (PDA) at 25 degrees C., 80% relative humidity (rh) for 14–21 days. Two agar plugs containing Pseudomassaria sp. ATCC 74411 was aseptically transferred to a 250 mL unbaffled flask containing 50 mL of seed medium having the following composition: dried corn steep, 2.0 g; tomato paste, 40.0 g; oat flour, 10.0 g; glucose, 10.0 g; agar, 4.0 g; $FeSO_4$—$7H_2O$, 0.01 g; $MnSO_4$—$4H_2O$, 0.01 g; $CuCl_4$—$2H_2O$, 0.0025 g; $CaCl_2$, 0.001 g; $H_3BO_3$, 0.0056 g; $(NH_4)_6Mo_7O_{24}$—$4H_2O$, 0.0019 g; $ZnSO_4$—$7H_2O$, 0.002 g; in 1 liter of 0.6 N HCl in distilled water. The culture was incubated on a shaker (220 rpm) at 25 degrees C. and 80% rh for 4 days, or until good growth was achieved. Frozen stocks of the seed culture are prepared by adding sterile glycerol to a final concentration of 10%. Storage is at −70 degrees C. One ml of a frozen stock, or plugs from a PDA plate, may be used to inoculate fresh seed medium for the fermentation.

(b) Production Culture of Pseudomassaria sp.

Two ml of a seed culture are used to inoculate 50 ml of production medium in 250 ml Erlenmeyer flasks. Incubation of the production flasks is at 25° C., 220 rpm, 80% rh for 21 days. Production medium contains D-mannitol, 100.0 g; NZ-Amine Type E, 33.0 g; Fidco yeast extract, 10.0 g; $(NH_4)_2SO_4$, 5.0 g; $KH_2PO_4$, 9.0 g and distilled water to 1 liter. No pH adjustment is necessary.

EXAMPLE 2

Isolation of Compound Ib

Whole broth from fermentation of Pseudomassaria sp. ATCC 74411 was extracted with methyl ethyl ketone. The extract (10 mL) was dried (250 mg) and loaded onto an LH 20 column eluting with MeOH. Fractions were collected in 15 mL volume. Fractions 11–20 were combined and dried to about 10 mg of a red residue. Analysis by analytical HPLC (55% acetonitrile/46% $H_2O$ with 0.1% trifluoroacetic acid) indicated that the pool contained one major peak. Thus, the 10 mg sample was loaded onto a semipreparative HPLC (Zorbax Rx-C8, 9.4×250 mm, 54% acetonitrile/46% $H_2O$ with 0.1% trifluoroacetic acid). The major peak eluted in fraction 54–57 (fractions were collected in 3 mL volume). The title compound crystallized as dark purple needles when stored in the cold room (4° C.).

$^1$H NMR($CH_2Cl_2$: 500 MHz): 1.50 (6H, s), 1.82(3H, d, 2.5 Hz), 1.88(3H, s), 3.65(2H, 7.0 Hz), 5.16(1H, dd, J=10.5, 1.0 Hz) 5.22(1H, dd, J=17.5, 1.0 Hz), 5.48(1H, m), 6.15(1H, dd, J=17.5, 10.5 Hz), 7.08(1H, m), 7.09(1H, m), 7.11(1H, m), 7.19(1H, m), 7.26(1H, dd, J=7.9, 0.7 Hz), 7.39(1H, dt, J=8.1, 0.8 Hz), 7.48(1H, d, 7.6 Hz), 7.63(1H, d, 2.8 Hz), 8.06(2H, b), 8.29(1H, b), 8.63(1H, b)

$^{13}$C NMR($CH_2Cl_2$: 125 MHz): 18.3, 26.0, 27.0, 31.2, 39.8, 100.0, 105.1, 111.2, 111.5, 112.1, 112.6, 118.9, 120.1, 120.4, 120.8, 122.5, 122.6, 125.0, 126.5, 127.3, 129.1, 134.2, 135.2, 135.5, 143.3, 145.9.

EXAMPLE 3

Isolation of Compound Ie.

Whole broth from fermentation of Pseudomassaria sp. ATCC 74411 was extracted with methyl ethyl ketone. The extract (500 ml) was dried (2 g) and applied to 400 ml flash silica gel column. The column was eluted with $CH_2Cl_2$ and then with increasing percentage of MeOH (1% acetic acid is added to the solvent mixture). Fractions eluted with 100% $CH_2Cl_2$ and 2.5% MeOH were pooled (1 g), and 10% of which was injected into a preparative HPLC (Zorbax Rx-C8, 21.2×250 mm, 55% acetonitrile in $H_2O$ with 0.1% TFA, 10 ml/min). The title compound eluted at 73 min.

$^1$H NMR ($CH_2Cl_2$: 500 Mhz): 1.50 (6H, s), 2.08 (3H, s), 5.16 (2H, m), 5.20 (2H, m), 6.13 (1H, dd, J=17.5 Hz, 10.5 Hz), 6.86 (1H, d, J=16.1 Hz), 7.04 (1H, J=16.1 Hz), 7.06 (1H, m), 7.17 (1H, m), 7.18 (1H, m), 7.23 (1H, bd, J=7.8 Hz), 7.37 (1H, m), 7.36 (1H, m), 7.53 (1H, bd, J=8.0 Hz), 7.68 (1H, m)

$^{13}$C NMR ($CH_2Cl_2$: 100 Mhz): 18.0, 27.2, 39.8, 100.0, 105.4, 111.0, 111.2, 112.2, 112.6, 118.0, 118.9, 120.4, 120.8, 120.9, 121.6, 122.3, 122.5, 124.6, 127.0, 127.6, 128.8, 133.6, 134.2, 135.2, 142.7, 143.3, 145.9.

EXAMPLE 4

Preparation of Compound Ia

To a solution of Compound Ib (10 mg, 0.020 mmol) dissolved in 2 mL of ethyl acetate was added 2 mL of $CH_2N_2$ in ethyl ether. The solution was stirred at room temperature for 20 min. The solvents were evaporated in a slow stream of nitrogen. The red residue was dissolved in 250 μL of MeOH and purified by HPLC (Zorbax Rx C-8, 0.94×25 cm; 60:40, $CH_3CN:H_2O$ 4 mL/min; rt 22–25 min). Fractions containing the product were lyophilized to provide pure title compound (9.2, 86%)

$^1$H NMR ($CD_2Cl_2$, 400 MHz): δ1.50 (6H, s), 1.84 (3H, d, J=1.2 Hz), 1.88 (3H, s), 3.65 (2H, d, J=7.1 Hz), 3.75 (3H, s), 3.80 (3H, s), 5.17 (1H, dd, J=1.1, 10.5 Hz), 5.21 (1H, dd, J=1.1, 17.5 Hz), 5.48 (1H, m), 6.13 (1H, dd, J=10.5, 17.5 Hz) ~7.11 (3H, m), 7.19 (1H, ddd, J=1.2, 7.0, 8.0 Hz), 7.28 (1H, d, J=7. Hz), 7.38 (1H, d, J=7.0 Hz), 7.39 (1H, d, J=7.0 Hz), 7.55 (1H, d, J=2.2 Hz), 8.30 (1H, s), 8.66 (1H, s).

$^{13}$C NMR ($CD_2Cl_2$, 100 MHz): 18.3, 26.0, 27.2, 27.5, 31.2, 39.8, 60.6, 61.2, 102.3, 106.3, 111.2, 112.6, 119.1, 119.5, 120.6, 121.0, 121.5, 122.4, 122.5, 122.8, 125.0, 127.3, 127.8, 130.3, 134.2, 135.0, 135.4, 142.8, 145.9, 160.9, 161.6, 183.8, 184.5 ppm.

EXAMPLE 5

Preparation of Compound Ic

To a solution of Compound Ib (12 mg, 0.024 mmol) dissolved in 1 mL of EtOH was added 1.8 mg of 10% Pd on carbon catalyst. The suspension was stirred under an atmosphere of $H_2$ gas after 2 cycles of vacuum degassing and $H_2$ saturation of the catalyst. The reaction was monitored by HPLC and was complete after 22 hrs. The catalyst was removed by filtration through a bed of Celite and the solvent removed by evaporation in a slow stream of air. This also serves to oxidize the hydroquinone form to the quinone. The red residue was dissolved in 250 μL of MeOH and purified by HPLC (Zorbax Rx C-8, 0.94×25 cm; 57:43, CH3CN:0.1% TFA 4 mL/min; rt 39–43 min). Fractions containing the product were lyophilized to provide pure title compound (10.5 mg, 87%)

$^1$H NMR (CD$_2$Cl$_2$, 400 MHz): δ0.84 (3H, t J=7.5 Hz), 1.05 (6H, d, J=6.1 Hz), 1.40 (6H, s), ~1.72 (5H, m), 2.91 (2H, dd, J=7.4, 8.0 Hz), ~7.11 (3H, m), 7.19 (1H, dd, J=7.3, 7.7 Hz), 7.25 (1H, d, J=7.9 Hz), 7.40 (1H, d, J=8.0 Hz), 7.49 (1H, d, J=7.2 Hz), 7.65 (1H, d, J=2.4 Hz), 8.10 (2H, s), 8.32 (1H, s), 8.62 (1H, s).

$^{13}$C NMR (CD$_2$Cl$_2$, 100 MHz): 10.4, 23.7, 28.5, 29.4, 30.3, 37.5, 38.2, 40.3, 100.9, 106.1, 111.9, 112.2, 113.2, 119.4, 120.7, 121.1, 121.6, 123.0, 123.1, 125.2, 127.1, 128.0, 130.0, 135.9, 136.1, 145.6 ppm.

EXAMPLE 6
Assay for Insulin Receptor Tyrosine Phosphorylation

CHO.T cells, which overexpress human insulin receptor (from Dr. R. A. Roth, Stanford University), are cultured in Hams F12 medium supplemented with 10% fetal calf serum, fungizone, penicillin and streptomycin at approximately 1.5×10$^5$ cells/well. The 96-well plates aew incubated for approximately 24 h at 37° C., which is when the cells reached confluency. The cells are washed with phosphate buffered saline (PBS) three times and then incubated in serum-free medium for 3 h at 37° C. Insulin and/or test compounds are added to the wells, and the cells are incubated for an additional 20 min at 37° C. The cells are washed three times with PBS and lysates are prepared. The lysates are transferred to a second 96 well plate. The wells of the second plate are precoated with monoclonal anti-insulin receptor antibody. Antibody is diluted to a final concentration of approximately 4 mcg/mL in 20 mM NaHCO$_3$, pH 9.6. Approximately 50 mcL of diluted antibody solution is added to each well. The lysates are incubated for 16 h at 4° C. to immunopurify the insulin receptor.

To detect the level of tyrosine phosphorylation of the insulin receptor captured on the plates, the washed plates are incubated for 5 h at 4° C. with monoclonal antiphoshotyrosine antibody conjugated to alkaline phosphatase (Transduction Laboratories). The unbound antibody is removed and chromogenic substrate of alkaline phosphotase is added to the wells. Signals are detected at 405 nm with a microtiter plate reader.

The cell culture conditions, preparation of lysates, and assays are essentially those described in B. Zhang et al., *J. Biol. Chem.*, Vol. 266, pages 990–996 (1991) and Zhang and Roth, *J. Biol. Chem.*, Vol. 267, pages 18320–18328, (1992).

EXAMPLE 7

Assay for Insulin Receptor Tyrosine Kinase Activity are CHO.T cells (approximately 1.5×10$^5$ cells/well) were cultured in Hams F12 medium supplemented with 10% fetal calf serum, fungizone, penicillin and streptomycin. The 96-well plates are incubated for approximately 24 h at 37° C., which is when the cells reached confluency. The cells are washed with phosphate buffered saline (PBS) three times and then incubated in serum-free medium for 3 h at 37° C. Insulin and/or test compounds are added to the wells, and the cells are incubated for an additional 20 min at 37° C. The cells are washed three times with PBS and lysates are prepared. The lysates are transferred to a second 96 well plate. The wells of the second plate are precoated with monoclonal anti-insulin receptor antibody. Antibody is diluted to a final concentration of approximately 4 mcg/mL in 20 mM NaHCO$_3$, pH 9.6. Approximately 150 mcL of diluted antibody solution is added to each well. The lysates are incubated for 16 h at 4° C. to immunopurify the insulin receptor.

To determine the insulin receptor tyrosine kinase activity, twenty microliters of the kinase reaction mixture (50 mM Hepes, pH 7.6, 150 mM NaCl, 5 mM MgCl$_2$, 5 mM MnCl$_2$, 0.1% Triton X-100, 1 mg/ml poly(Glu:Tyr)(4:1), 2 μCi of carrier-free [γ-$^{32}$P]ATP) is added to each well of the 96-well plates and the incubation is continued at 25° C. for 40 min. The reaction is terminated by addition of 50 μl 100 mM phosphoric acid. The mixture is transferred to Multiscreen PH plates and washed. The radioactivities associated with the wells are determined using a Topcount. The insulin receptor tyrosine kinase activities stimulated by test agents are compared to that stimulated by insulin.

EXAMPLE 8
In Vivo Assay for Oral Anti-hyperglycemic Activity

Genetically altered obese diabetic mice (db/db) (male, 7–9 weeks old) are housed (7 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch BasicGlucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed orally by gavage with either vehicle (containing 5% ethanol, 0.2% Tween-20 in water) or test compound at 5 or 25 mg/kg in a volume of 10 ml/kg. Blood is sampled from the tail vein hourly for 4 hours and at 24, 30 h post-dosing and analyzed for blood glucose concentrations. Food is withdrawn from 0–4 h post dosing and reintroduced thereafter. Individual body weights and mean food consumption (each cage) are also measured after 24 h. Significant differences between groups (comparing drug-treated to vehicle-treated) are evaluated using Student t-test.

What is claimed is:

1. A method of treating or preventing the onset of diabetes mellitus in an animal which comprises administering to said animal a therapeutically effective amount of an asterriquinone of Formula I:

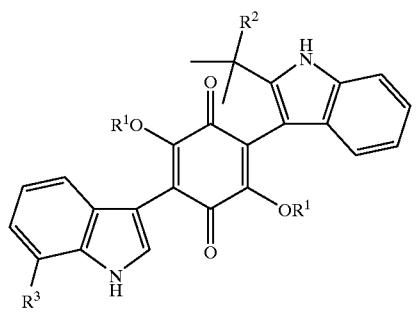

wherein
R$^1$ is hydrogen or methyl;
R$^2$ is —CH$_2$CH$_3$ or —CH=CH$_2$;
R$^3$ is —CH=CH—C(CH$_3$)=CH$_2$; —CH$_2$—CH=C(CH$_3$)$_2$ or —CH$_2$—CH$_2$—CH(CH$_3$)$_2$;
or a pharmaceutically acceptable salt thereof.

2. A method of reducing the blood glucose level in an animal in need of such reduction which comprises administering to said animal a glucose reducing effective amount of the asterriquinone of Formula I, as defined in claim 1, or a pharmaceutically acceptable salt thereof.

3. A method of treating Type I diabetes mellitus in an animal which comprises administering to said animal a therapeutically effective amount of an asterriquinone of Formula I, as defined in claim 1, or a pharmaceutically acceptable salt thereof.

4. A method of treating, preventing, suppressing, or controlling conditions associated with insulin resistance or insulin deficiency in an animal, wherein said conditions are selected from atherosclerosis, hypertension, lipid disorders, and polycystic ovarian syndrome, which method comprises administering to said animal a therapeutically effective amount of an asterriquinone of Formula I, as defined in claim 1, or a pharmaceutically acceptable salt thereof.

5. A method of treating or preventing the onset of diabetes mellitus in an animal which comprises administering to said animal a therapeutically effective amount of an asterriquinone having the following formula:

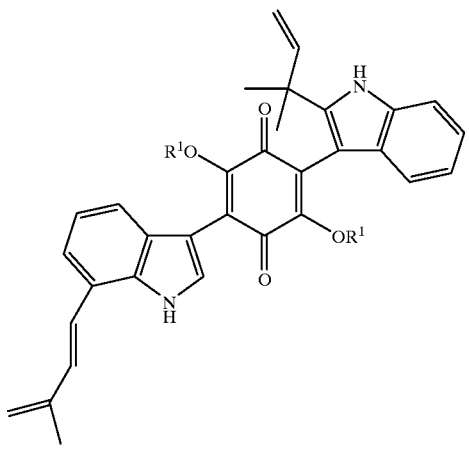

wherein R1 is H or methyl, or a pharmaceutically acceptable salt thereof.

6. A method of reducing the blood glucose level in an animal in need of such reduction which comprises administering to said animal a glucose reducing effective amount of the asterriquinone defined in claim 5, or a pharmaceutically acceptable salt thereof.

7. A method of treating Type I diabetes mellitus in an animal which comprises administering to said animal a therapeutically effective amount of the asterriquinone, as defined in claim 5, or a pharmaceutically acceptable salt thereof.

8. A method of treating, preventing, suppressing, or controlling conditions associated with insulin resistance or insulin deficiency in an animal, wherein said conditions are selected from atherosclerosis, hypertension, lipid disorders, and polycystic ovarian syndrome, which method comprises administering to said animal a therapeutically effective amount of the asterriquinone as defined in claim 5, or a pharmaceutically acceptable salt thereof.

* * * * *